United States Patent [19]

Sayles

[11] 4,391,993
[45] Jul. 5, 1983

[54] THERMOLYSIS OF TETRAALKYLAMMONIUM BOROHYDRIDES TO BIS(TETRAALKYLAMMONIUM) DECAHYDRODECABORANES

[75] Inventor: David C. Sayles, Huntsville, Ala.

[73] Assignee: The United States of America as represented by the Secretary of the Army, Washington, D.C.

[21] Appl. No.: 348,538

[22] Filed: Feb. 12, 1982

[51] Int. Cl.$^3$ .............................................. C07F 5/02
[52] U.S. Cl. ........................................ 568/4; 422/130; 422/202; 422/205; 422/225; 568/3; 568/5
[58] Field of Search ............... 568/3, 4; 422/130, 205, 422/202, 225

[56] References Cited

U.S. PATENT DOCUMENTS

| | | | |
|---|---|---|---|
| 2,557,910 | 6/1951 | Green | 422/205 X |
| 3,313,838 | 4/1967 | Rozzi | 422/205 X |
| 3,525,593 | 8/1970 | Thompson | 422/130 |
| 4,338,289 | 7/1982 | Shore et al. | 568/4 X |

*Primary Examiner*—Helen M. S. Sneed
*Attorney, Agent, or Firm*—William G. Gapcynski; Arthur I. Spechler; Jack W. Voigt

[57] ABSTRACT

Disclosed is an improved method and the thermolysis equipment setup for converting tetraethylammonium tetrahydridoborane to bis(tetraethylammonium) decahydrodecaborane by a thermolysis reaction which increases the yield in the range between about 22% to 64%, and, perhaps higher. The heat transfer control is maintained by employing triethylamine borane in the reaction mixture between about 175° C. and 186° C. for a reaction time from about 1 hour to about 2.5 hours. The disclosed thermolysis procedure is successful in dissipating a major portion of the exothermic heat. The control of the generated heat serves to minimize the formation of the byproduct bis(tetraethylammonium) dodecahydrododecaborane while increasing the yield of the desired product, bis(tetraethylammonium) decahydrodecaborane.

5 Claims, 2 Drawing Figures

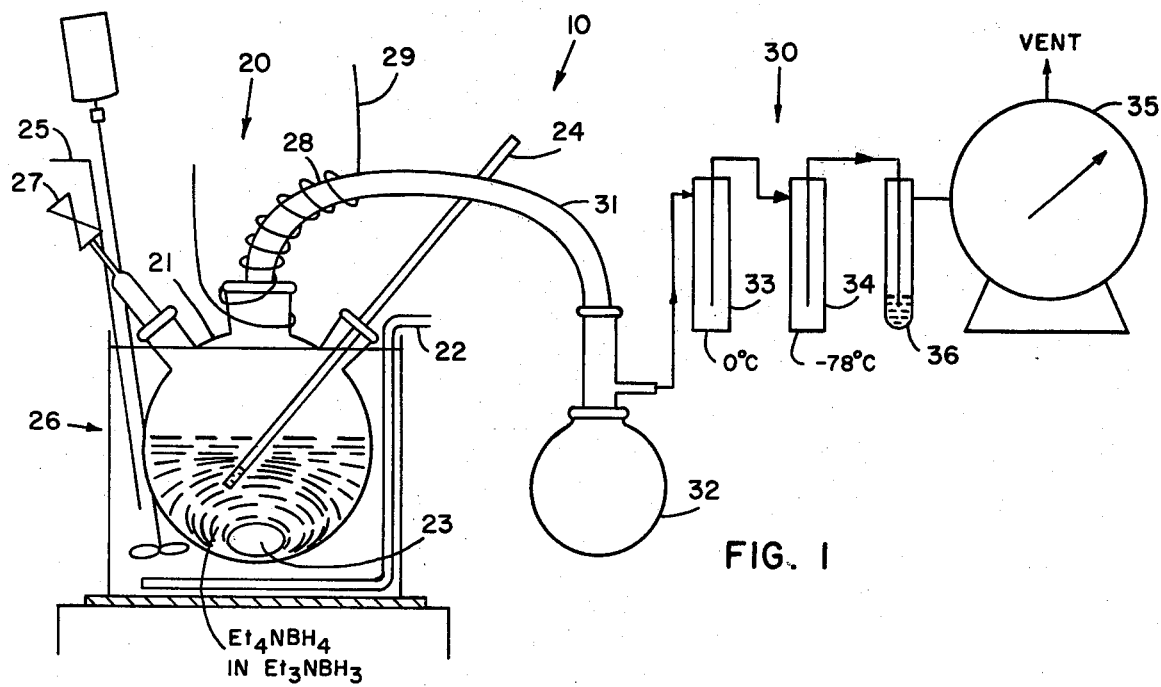
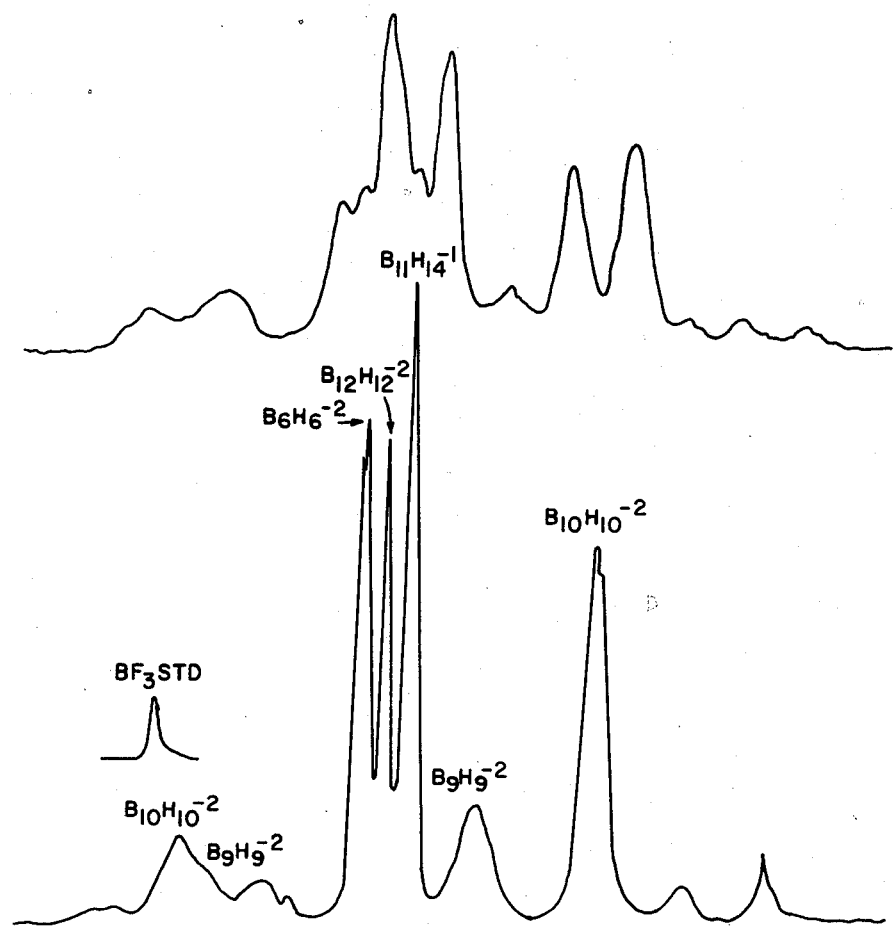

THERMOLYSIS OF TETRAALKYLAMMONIUM BOROHYDRIDES TO BIS(TETRAALKYLAMMONIUM) DECAHYDRODECABORANES

DEDICATORY CLAUSE

The invention described herein may be manufactured, used, and licensed by or for the Government for governmental purposes without the payment to me of any royalties thereon.

BACKGROUND OF THE INVENTION

The pyrolysis of thermolysis of tetraethylammonium borohydride, as described in my prior U.S. Pat. No. 4,150,057, Apr. 17, 1979, "Method for Preparation of a Carboranyl Burning Rate Accelerator Precursor", into bis(tetraethylammonium) decahydrodecaborane ($[Et_4N]_2B_{10}H_{10}$) is only accomplished in relatively low yields because of the difficulties involved in controlling the thermolysis reaction. As a result, a considerable quantity of bis(tetraethylammonium) dodecahydrododecaborane ($[Et_4N]_2B_{12}H_{12}$) is produced instead of the desired product, bis(tetraethylammonium) decahydrodecaborane. Because of the low yield of the desired product, three other processes have been devised which involve the use of different starting materials to produce a common ingredient, diborane, which is subsequently thermolyzed into decaborane. The decaborane is the essential material for the synthesis of n-hexylcarborane and carboranylmethyl propionate.

Advantageous would be a process which would obviate the undesirable features of the three processes. Such a process for the synthesis of carboranes would be particularly attractive if it offered several major advantages over the other three processes; namely, such as, (a) bypassing the flammable and toxic chemical intermediates, namely, diborane and decaborane; (b) being of low cost; (c) producing a higher yield of an intermediate involved in the production of carboranes.

Therefore, an object of this invention is to provide an improved process for the thermolysis of tetraalkylammonium borohydride to bis[tetraalkylammonium] decahydrodecaboranes.

Another object of this invention is to provide an improved process that yields a higher percentage of bis(tetraalkylammonium) decahydrodecaboranes from the thermolysis of tetraalkylammonium borohydride.

SUMMARY OF THE INVENTION

The thermolysis procedure of this invention is successful in producing a high yield of bis(tetraethylammonium) decahydrodecaborane from tetraethylammonium borohydride. The success of the thermolysis procedure is attributed to the use of boron-based solvents, such as, triethylamine borane ($Et_3NBH_3$) (wherein $Et=C_2H_5$), to control the thermolysis reaction in dissipating a major portion of the exothermic heat. The control of the generated heat serves to minimize the formation of the undesired byproduct, bis(tetraethylammonium) dodecahydrododecaborane.

Thermolysis temperatures of 180° C. are near optimum since this permits shortened reaction times and lesser quantities of triethylamine borane being required to produce maximum yields of $(Et_4N)_2B_{10}H_{10}$ and minimum yields of any $B_{12}H_{12}^{(2-)}$ derivative.

BRIEF DESCRIPTION OF THE DRAWING

FIG. 1 of the drawing depicts the equipment setup for the thermolysis of tetraethylammonium tetrahydroborate into bis(tetraethylammonium) decahydrodecaborane.

FIG. 2 of the drawing depicts the nuclear magnetic resonance ($B^{11}$) spectrum of thermolysis products.

DESCRIPTION OF THE PREFERRED EMBODIMENT

The thermolysis reaction of this invention results in a high yield of $(Et_4N)_2B_{10}H_{10}$ which is achieved through the control of the heat transfer between a boron-based solvent, such as, triethylamine borane ($Et_3NBH_3$) and the pyrolyzed reactant, tetraethylammonium borohydride (Other acceptable names for this reactant are tetraethylammonium tetrahydridoborane and tetraethylammonium tetrahydroborate). The yield by the process of this invention is about 64% when the reaction is carried out using $Et_3NBH_3$ as solvent as compared to about 22% for the reaction as described in my U.S. Pat. No. 4,150,057. This lower efficiency reaction was carried out in an evacuated and sealed stainless steel reactor which was heated to 185° C., and this temperature was maintained for 18 hours.

The thermolysis procedure of this invention is successful in dissipating a major portion of the exothermic heat. The precise control of the generated heat serves to minimize the formation of an undesired byproduct, bis(tetraethylammonium) dodecahydrododecaborane.

The following chemical equation depicts the thermolysis reaction:

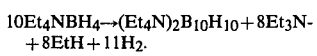

$$10Et_4NBH_4 \rightarrow (Et_4N)_2B_{10}H_{10} + 8Et_3N + 8EtH + 11H_2.$$

The thermolysis reaction involved 50 grams of $Et_4NBH_4$ in 25–200 grams of $Et_3NBH_3$ (i.e., a mole ratio from about 0.3 to 1.0 to 0.2 to 4.0 respectively). The thermolysis reaction was carried out under an inert atmosphere of nitrogen at a pressure somewhat above one atmosphere. The equipment (Setup 10) for the thermolysis reaction is shown in FIG. 1 wherein the reactor system 20 and the recovery system 30 are shown is a preferred arrangement. The reactor vessel 21 consists of a three-neck, round bottom flask, heated by an electric immersion heater 22 for the heating oil system 26, and provided with a magnetic stirrer including a tefloncovered stirring bar magnet 23 in the reactor vessel. An immersion thermometer 24 is shown in position for measuring the temperature of the reaction mixture. The reaction vessel is also provided with an inert gas supply system 27 for maintaining an inert atmosphere during thermolysis reaction. The heating oil system 26 (including a container for the heating oil medium, stirrer, and immersion heater 22) is employed to maintain the proper thermolysis reaction temperature, and the hot oil control 25 is employed to maintain the heating oil medium within the desired temperature range.

The gases which are evolved are passed through a heated tube 28 to minimize any refluxing action from taking place. Heating tape 29 is shown wrapped around the tube for heating the tube 28 as described. The evolved gases are then passed through an air-cooled passageway 31 and then to a room temperature receiver 32. Vapor traps (33 and 34) are cooled to 0° C. and −78° C., respectively, for collecting the condensable gases, and the non-condensable gases are measured by means of a wet gas meter 35. A back pressure regulator 36 (mercury bubbler) is shown in communication with the wet test meter.

The triethylamine which is formed in the reaction is condensed out of the gaseous byproducts in the −78° C. cold trap. The condensate also is found to contain as much as 50% triethylamine borane. The non-condensable gaseous effluents, consisting of ethane and hydrogen, are measured by a wet gas meter. When chemical reaction ceases, the residue in the reactor is rapidly cooled to room temperature through the removal of the heater.

The residue, remaining after the thermolysis reaction is carried out, is filtered from the remaining triethylamine borane solvent. The filter cake which contains the $(Et_4N)_2B_{10}H_{10}$ is thoroughly washed with hexane to remove any triethylamine borane. The hexane adhering to the filter cake is thoroughly dried in a vacuum desiccator.

The yields of $B_{10}H_{10}{}^{(2-)}$ are estimated from the weight of the product and from the estimates of $B_{10}H_{10}{}^{(2-)}$ and the byproduct which were obtained by infrared analyses, Nuclear Magnetic Resonance (NMR), and liquid chromatography.

The upper spectrum in FIG. 2 depicts the hydrogen-boron coupling, and the lower spectrum depicts the proton decoupled spectrum. These data were interpreted using boron trifluoride as the standard. The relative yields of $(Et_4N)_2B_{10}H_{10}$ and the byproducts were obtained by determining the area ratios for each compound. The adverse nuclear Overhauser effects were kept at a minimum by decoupling the system at the appropriate proton field strength.

Thermolysis temperatures of 180° C. were found to be near optimum. At this temperature, the reaction times could be shortened and lesser quantities of triethylamine borane could be used to produce maximum yields of $(Et_4N)_2B_{10}H_{10}$ and minimum yields of any $B_{12}H_{12}{}^{(2-)}$ derivative. These data are summarized in Table I.

TABLE I

| THERMOLYSIS OF TETRAETHYLBOROHYDRIDES | | | | |
|---|---|---|---|---|
| | RUNS | | | |
| | 1 | 2 | 3 | 4 |
| Tetraethylborohydride (Moles) | 0.345 | 0.345 | 0.345 | 0.345 |
| Triethylamine Borane (Moles) | 0.87 | 1.067 | 0.6 | 0.217 |
| Temperature (Bath) (°C.) | 175–186 | 186 | 186 | 186 |
| Temperature (Reaction Mix) (°C.) | 175–182 | 183 | 183 | 186 |
| Reaction Time (Hrs) | 1–2 | 1.5 | 1.5 | 2.5 |
| Off Gas (L) (g) | 8.14–14.8 | 16.7 | 15.0 | 13.6 |
| (%) | 101 | 114 | 102 | 92 |
| Triethylamine Borane (Moles) | 0.63 | 0.74 | 0.53 | 0.16 |
| Triethylamine (%) | — | 114 | — | 81.5 |
| Product (Weight) (g) | 13.0 | 15.0 | 13.5 | 14.0 |
| (%) | 100 | 115 | 104 | 108 |
| Yield $(Et_4N)_2B_{10}H_{10}$ (%) | 31 | 34 | 36 | 64 |

The maximum yield of $(Et_4N)_2B_{10}H_{10}$ was obtained in Run 4. In this run, the triethylamine borane had been reduced to 50% of the weight of $Et_4NBH_4$. This quantity of solvent was only adequate to wet the solid material contained in the reactor. A considerable amount of time (75 min) was required to raise the temperature of the reaction mixture to 180° C. Off-gassing started below 100° C. Some physical changes occurred as the thermolysis proceeded.

Reasonably-optimized conditions were used in Run 4. Based on infrared analysis, the yield of $(Et_4N)_2B_{10}H_{10}$ was substantially above 64%.

Thus, thermolysis of tetraalkylammonium borohydrides to bis(tetraalkylammonium) decahydrododecaboranes in accordance with this invention, differs from previous inventions in the following aspects: (a) There are four prior art processes which have been devised for the synthesis of n-hexylcarborane and carboranylmethyl propionate. Three of these involve the use of different starting materials to produce diborane. The diborane is then thermolyzed into decaborane. Whereas, the fourth process involves the thermolysis of tetraethylammonium borohydride. The yield of this thermolysis reaction was so low (22%) as to make this process economically unfeasible; however, the process of this invention which includes the use of the solvent, triethylamine borane, as the means for heat transfer, results in increasing the yield to 64%, and the possibility still exists of raising the yield to a still higher level.

The process of this invention for the synthesis of carboranes has several attractive advantages over the other three processes; namely, (a) bypasses the flammable and toxic intermediates, diborane and decaborane; (b) lower cost; (c) higher yield of the intermediate involved in the production of carboranes. Additionally, the attractive advantage over the prior art for the thermolysis process of tetraalkylammonium borohydrides to bis(tetraalkylammonium) decahydrodecaboranes is recognized which relates to higher yield of desired product, less yield of undesired byproduct, and lower costs for producing the compound involved in the production of the widely used carborane catalyst, n-hexylcarborane. Additionally, the process of this invention is useful in the production of carboranylmethyl propionate which is a necessary ingredient for the manufacture of the ultrahigh-burning rate, composite-modified, double-base propellant which is being developed for use in future advanced interceptors.

This process for the synthesis of carboranylmethyl propionate can be summarized as follows:

$NaBH_4 + Et_4NCl \longrightarrow Et_4NBH_4 +$

HEAT using $Et_3NBH_3$ solvent $\longrightarrow [Et_4N]_2 B_{10}H_{10} +$ $R_2S/H^+ \longrightarrow [R_2S]_2B_{10}H_{10} + HC\!:\!C.CH_2.O_2C.Et \longrightarrow$

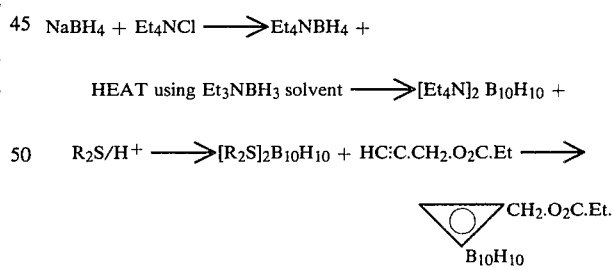

I claim:
1. A process for the thermolysis reaction of tetraethylammonium borohydride to yield bis(tetraalkylammonium) decahydrodecaborane which comprises:
  (i) combining $Et_4NBH_4$ in a mole ratio from about 0.3 to 1.0 with a boron-based solvent $Et_4NBH_3$ in a mole ratio from about 0.2 to 4.0 to form a reaction mixture, (wherein Et is $C_2H_5$), in a thermolysis reactor vessel having a plurality of outlets for various functions including an outlet for the introduction of reactants and an inert gas, an outlet through which the reaction temperature is monitored, and an outlet for discharging reaction products to a recovery system, said reactor vessel provided with an immersion oil heating means for heating including a temperature control means for controlling the reaction temperature, a means for maintaining an inert atmosphere of nitrogen over said reaction mixture, and a temperature measuring means for measuring temperature of the reaction mixture;

(ii) connecting one of said outlets of said reactor vessel to a recovery system comprised of a tube member having a heated tube section on one end to prevent any reflux action to said reaction vessel, and said tube member having an air-cooled condenser section on the other end of said tube member, said air-cooled condenser section being connected to a distillate receiver, said distillate receiver having a discharge outlet that is connected in series with a 0° C. cooled trap, a −78° C. cooled trap, a back pressure regulator, and a wet test gas meter; said cooled traps for collecting the condensable gases and said wet test gas meter for measuring the non-condensable gases;

(iii) introducing and maintaining an inert atmosphere of nitrogen in said reactor vessel and said recovery system;

(iv) heating said reaction mixture while stirring and controlling said reacting mixture to maintain a thermolysis temperature between about 175° C. and 186° C. for a reaction time from about 1 to about 2.5 hours until chemical reaction ceases;

(v) removing said reactor vessel from said immersion oil heating means, and cooling the residue in said reactor vessel to room temperature;

(vi) filtering off any remaining triethylamine borane solvent and recovering the filter cake;

(vii) washing said filter cake with hexane to remove any additional triethylamine borane; and (viii) drying said washed filter cake to remove any hexane adhering to said filter cake to yield $(Et_4N)_2B_{10}H_{10}$.

2. The process as set forth in claim 1 wherein said $Et_4NBH_4$ is reacted in said $Et_3NBH_3$ solvent in a mole ratio of about 0.345 of said $Et_4NBH_4$ to about 0.87 of said $Et_3NBH_3$ and wherein said thermolysis temperature is maintained between about 175° C. and 186° C. for a reaction time of about 1–2 hours to yield said $(Et_4N)_2B_{10}H_{10}$ in a percent yield of about 31.

3. The process, as set forth in claim 1, wherein said $Et_4BNH_4$ is reacted in said $Et_3NBH_3$ solvent in a mole ratio of about 0.345 of said $Et_4NBH_4$ to about 1.067 of said $Et_3NBH_3$, and wherein thermolysis temperature is maintained at about 183° C. for a reaction time of about 1.5 hours to yield said $(Et_4N)_2B_{10}H_{10}$ in a percent yield of about 34.

4. The process, as set forth in claim 1, wherein said $Et_4NBH_4$ is reacted in said $Et_3NBH_3$ solvent in a mole ratio of about 0.345 of said $Et_4NBH_4$ to about 0.6 of said $Et_3NBH_3$, and wherein said thermolysis temperature is maintained at about 183° C. for a reaction time of about 1.5 hours to yield said $(Et_4N)_2B_{10}H_{10}$ in a percent yield of about 36.

5. The process, as set forth in claim 1, wherein said $Et_4NBH_4$ is reacted in said $Et_3NBH_3$ solvent in a mole ratio of about 0.345 of said $Et_4NBH_4$ to about 0.217 of said $Et_3NBH_3$, and wherein thermolysis temperature is maintained at about 186° C. for a reaction time of about 2.5 hours to yield said $(Et_4N)_2B_{10}H_{10}$ in a percent yield of about 64.

* * * * *